United States Patent [19]

Pingleton et al.

[11] Patent Number: 5,312,432
[45] Date of Patent: May 17, 1994

[54] PERCUTANEOUSLY INSERTABLE, NEEDLE-SIZED TISSUE RETRACTOR AND SYSTEM

[75] Inventors: Edward D. Pingleton; Paul G. Thomson, both of Fillmore, Ind.

[73] Assignee: Vance Products Inc., Spencer, Ind.

[21] Appl. No.: 877,644

[22] Filed: May 1, 1992

[51] Int. Cl.$^5$ .............................................. A61B 17/00
[52] U.S. Cl. ...................................................... 606/205
[58] Field of Search ........................... 606/205–211; 128/751–755; 604/3–6

[56] References Cited

U.S. PATENT DOCUMENTS

| | | | |
|---|---|---|---|
| 86,016 | 1/1869 | Howell | 606/207 |
| 4,122,856 | 10/1978 | Mosior et al. | 606/170 |
| 4,655,219 | 4/1987 | Petruzzi | 606/206 |
| 4,830,002 | 5/1989 | Semm | 606/207 |
| 4,898,157 | 2/1990 | Messroghli et al. | 606/208 |
| 4,944,741 | 7/1990 | Hasson | 606/207 |
| 5,002,557 | 3/1991 | Hasson | 606/191 |
| 5,133,736 | 7/1992 | Bales, Jr. et al. | 606/170 |

*Primary Examiner*—Stephen C. Pellegrino
*Assistant Examiner*—William Lewis
*Attorney, Agent, or Firm*—Richard J. Godlewski

[57] ABSTRACT

A percutaneously insertable, needle-sized retractor and system for grasping and retracting tissue in a cavity of a patient. The system comprises a needle-sized trocar sheath having an outside diameter in a range from 10 to 22 gauge, a pointed distal end stylet insertable into the trocar sheath, and a tissue-grasping retractor also insertable through the trocar sheath. The stylet is inserted through the trocar sheath with the pointed distal end extending therefrom. The trocar sheath and stylet are then inserted through a patient's skin and subtending tissue and organs into a desired cavity. When the trocar sheath is inserted, the stylet is removed and the tissue grasping retractor inserted through the sheath and into the cavity. A retaining cap at the proximal end of the sheath fixedly positions the retractor with respect to the trocar sheath while a retention flange positioned around the outside surface of the sheath fixedly positions the sheath with respect to the patient. Thus, the tissue grasping retractor and system grasps and retracts tissue during a minimally invasive procedure with minimal trauma to the patient.

5 Claims, 2 Drawing Sheets

PERCUTANEOUSLY INSERTABLE, NEEDLE-SIZED TISSUE RETRACTOR AND SYSTEM

TECHNICAL FIELD

This invention relates to surgical instruments and particularly to a needle-sized tissue retractor and system that are percutaneously inserted into a cavity of a subject.

BACKGROUND OF THE INVENTION

Minimally invasive endoscopic surgery is performed using two or more trocar sheaths for gaining access to a cavity of a patient. These trocar sheaths provide access to the surgical site for various medical instruments such as forceps, scissors, and scopes. The advantages of endoscopic surgery over traditional, open surgery include decreased trauma for the patient, smaller wounds and less scarring, faster healing and recovery time, and decreased risk of infection.

A problem presented by endoscopic surgical procedures is that a surgeon has no direct visualization of the surgical site. Instead, visualization of the surgical site is by a video camera and monitor. The surgeon uses medical devices inserted through access sheaths to manipulate tissue adjacent the surgical site for lifting tissue out of the line of sight. A solution to this problem is the use of an additional access sheath for inserting forceps or a grasper to the surgical site for retracting tissue. A limitation of using these sheaths, however, is that the trocar sheaths normally range in size from 3 to 10 mm and leave deep, cylindrical wounds where a significant bulk of tissue is removed. As a result, surgeons tend to use as few access sheaths as possible.

In endoscopic surgical procedures, the surgeon does not directly manipulate tissue as in traditional, open surgery. To perform the task of moving tissue aside and away from the surgical site, the surgeon or surgical assistants must insert forceps or a grasper through an access sheath, grasp the desired tissue, move the tissue aside, and then manually maintain the position of the grasper and tissue for the duration of a surgical procedure. A problem with manually stabilizing medical devices such as a grasper is that the surgeon or surgical assistants lack control over the grasper and tissue due to muscle fatigue or inadvertent movement over the duration of the procedure. Another problem with the use of these known medical devices for repositioning tissue is that one or both hands of each surgeon or surgical assistant are occupied. When the surgeon or surgical assistant must release a device prematurely to perform a more urgent task, as often happens during surgery, the tissue returns to its original position. As a result, the surgeon's line of sight or access to the surgical site is obstructed, and operative time is extended.

SUMMARY OF THE INVENTION

The foregoing problems are solved and a technical advance is achieved in an illustrative tissue retractor that is percutaneously inserted into a cavity of a patient through a needle-sized trocar sheath. The retractor comprises an elongated member and a tissue grasper positioned about the distal end of the elongated member. The grasper has open and closed positions for engaging and releasing tissue. The grasper in the closed position and the elongated member are sized for insertion through a needle-sized trocar sheath having an outside diameter in a range of 10 to 22 gauge. The needle-sized trocar sheath and retractor advantageously minimize trauma to the patient and the bulk associated with commonly used trocar sheaths ranging in size from 3 to 10 mm. The retractor also includes an easily operated handle that is positioned about the proximal end of the elongated member for operating the grasper between the open and closed positions.

The elongated member of the retractor includes an outer cannula and an inner rod extending through the passage of the outer cannula. The grasper includes pivotedly interconnected jaws operable between the open and closed positions with the first jaw connected to the distal end of the outer cannula and the second jaw connected to the distal end of the inner rod. The handle includes an enclosure having a cavity therein and a piston slidably positioned in the cavity for operating the grasper between the open and closed positions. The proximal end of the outer cannula is connected to the enclosure, whereas the piston is connected to the proximal end of the inner rod. Retaining tubes are positioned on the outer cannula to advantageously fixedly position the cannula with respect to the enclosure. The handle further includes a spring positioned in the cavity that engages both the enclosure and the piston for maintaining the grasper in one of the open and closed position. The elongated member of the retractor further includes an outer sheath of, for example, nylon. The outer cannula and inner rod are inserted in the passage of the outer sheath. The outer sheath is connected to the handle for easy percutaneous insertion of the elongated retractor member into the cavity of a patient.

The retractor system includes the tissue retractor and the needle-sized trocar sheath through which the tissue retractor is extended therethrough. The retractor system further comprises a trocar stylet insertable through the passage of the trocar sheath and stylet into the cavity of the patient. The trocar stylet includes a pointed distal end that extends from the distal end of the sheath when the stylet is inserted through the passage of the sheath. The sheath further includes a retention cap positioned about the proximal end of the sheath. The cap includes a second passage extending therethrough that communicates with the passage of the sheath. The cap also includes a seal positioned about the passage of the cap for fixedly positioning the retractor when inserted through the passage of the cap and sheath. This advantageously allows the physician to percutaneously grasp and retract tissue and fixedly position the retractor and tissue in a desirable position so as not to interfere with the line of sight during a minimally invasive endoscopic procedure. The retractor system further comprises a retention flange that is positioned around the outside surface of the sheath and is movable and fixedly positionable therealong. The retention flange is utilized to advantageously fixedly position the sheath and retractor with respect to the surface tissue of the patient.

DETAILED DESCRIPTION

Figure 1:
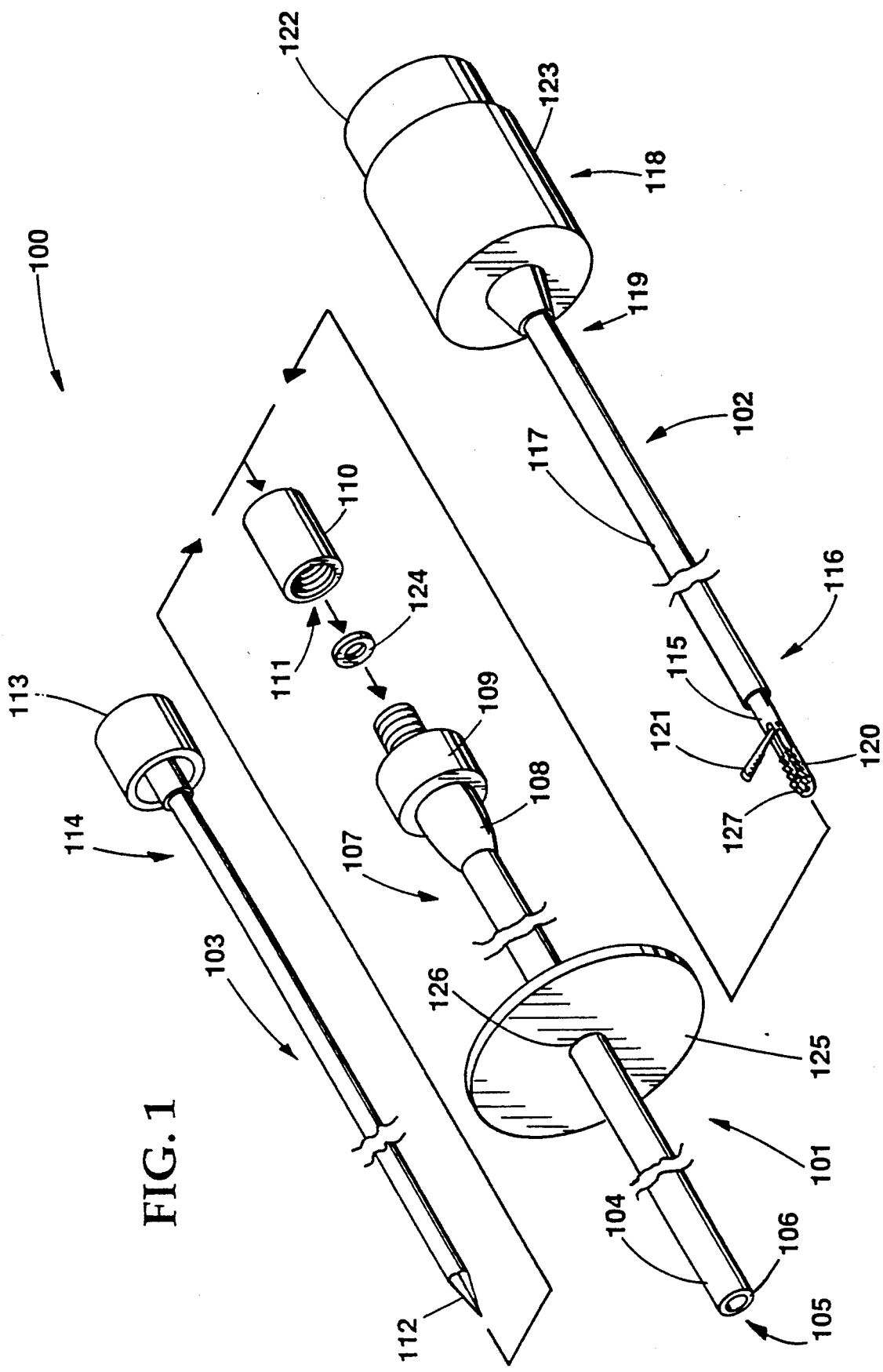
FIG. 1 depicts an illustrative percutaneously insertable, needle-sized retractor and system of the present invention.

Depicted in FIG. 1 is an illustrative percutaneous retractor system 100 comprising needle-sized trocar sheath 101, tissue retractor 102, and trocar stylet 103 for percutaneous insertion into the cavity of a patient. The trocar sheath comprises a polytetrafluoroethylene radiopaque material tube 104 having passage 105 extending longitudinally therethrough. Tube 104 has an outside diameter in a range of 10 to 22 gauge (0.028" to 0.134") and is approximately 13 cm in length. Preferably, tube 104 has an 8 French (0.105") outside diameter and a wall 106 thickness of approximately 0.016". Fixedly attached using, for example, medical grade adhesive about proximal end 107 of the tube are well-known male and female Luer lock connector adapters 108 and 109. Also positioned about the proximal end of the tube is retention cap 110 threadably engaging female connector adapter 109. Passage 111 extends through the retention cap and connector adapters to communicate with passage 105 of the polytetrafluoroethylene tube. Trocar stylet 103 is inserted through passages 105 and 111 of the tube and retention cap. When the trocar stylet is fully inserted in tube 104, pointed distal end 112 of the stylet extends distally from passage 105 of the tube. The trocar sheath with the pointed distal end of the stylet extending therefrom is then percutaneously inserted into the cavity of a patient through the skin and subtending tissue and organs. The trocar stylet stiffens the sheath for advancement through the skin and subtending tissues and organs. A well-known connector cap 113 is fixedly positioned about a proximal end 114 of the stylet with, for example, medical grade adhesive for positioning and manipulating the stylet with respect to the trocar sheath. The trocar stylet preferably comprises a stainless steel material rod approximately 17 cm in length with an outer diameter of approximately 0.068". The distal end of the rod is ground to a point for easy insertion into the cavity of a patient.

When the trocar stylet and sheath are inserted into the cavity of a patient, the stylet is removed from the passage of the sheath. Tissue retractor 102 is then inserted through the passage of the trocar sheath and into the cavity of the patient. The retractor includes grasper 115 positioned at distal end 116 of elongated member 117. Tissue retractor 102 also comprises push-button handle 118 attached about proximal end 119 of elongated member 117. Handle 118 is grasped by the middle and index fingers along with the thumb of the physician to operate pivotedly interconnected jaws 120 and 121 of grasper 115 between open and closed positions. Jaws 120 and 121 have well-known alligator teeth for grasping tissue or, alternatively, a well-known hounds tooth configuration. Normally, the grasper is maintained in the closed position with jaws 120 and 121 engaging one another. The jaws of the grasper are operated to the open position by the physician pressing push-button piston 122 of the handle which slidably moves in enclosure 123 of the handle. Retaining cap 110 of the trocar sheath includes seal 124 positioned about passageway 111, which is compressed to engage elongated member 117 of the retractor. This is accomplished by the physician turning retention cap 110, compressing the seal, and fixedly positioning the retractor in passages 105 and 111 of the trocar sheath and retention cap.

The retractor system further comprises a well-known retention flange 125, such as the Molnar retention disk commercially available from Cook Urological, Incorporated, Spencer, Ind. The disk includes passage 126 of which trocar sheath tube 104 is inserted therethrough. The disk is moved along the length of the tube to engage the surface of the skin and fixedly position the trocar sheath with respect to the cavity. With the retention cap fixedly positioning the grasper, and the retention flange fixedly positioning the trocar sheath with respect to the surface tissue of the patient, the grasper can effectively grasp, retract, and fixedly position tissue during a minimally invasive endoscopic procedure.

Figure 2:
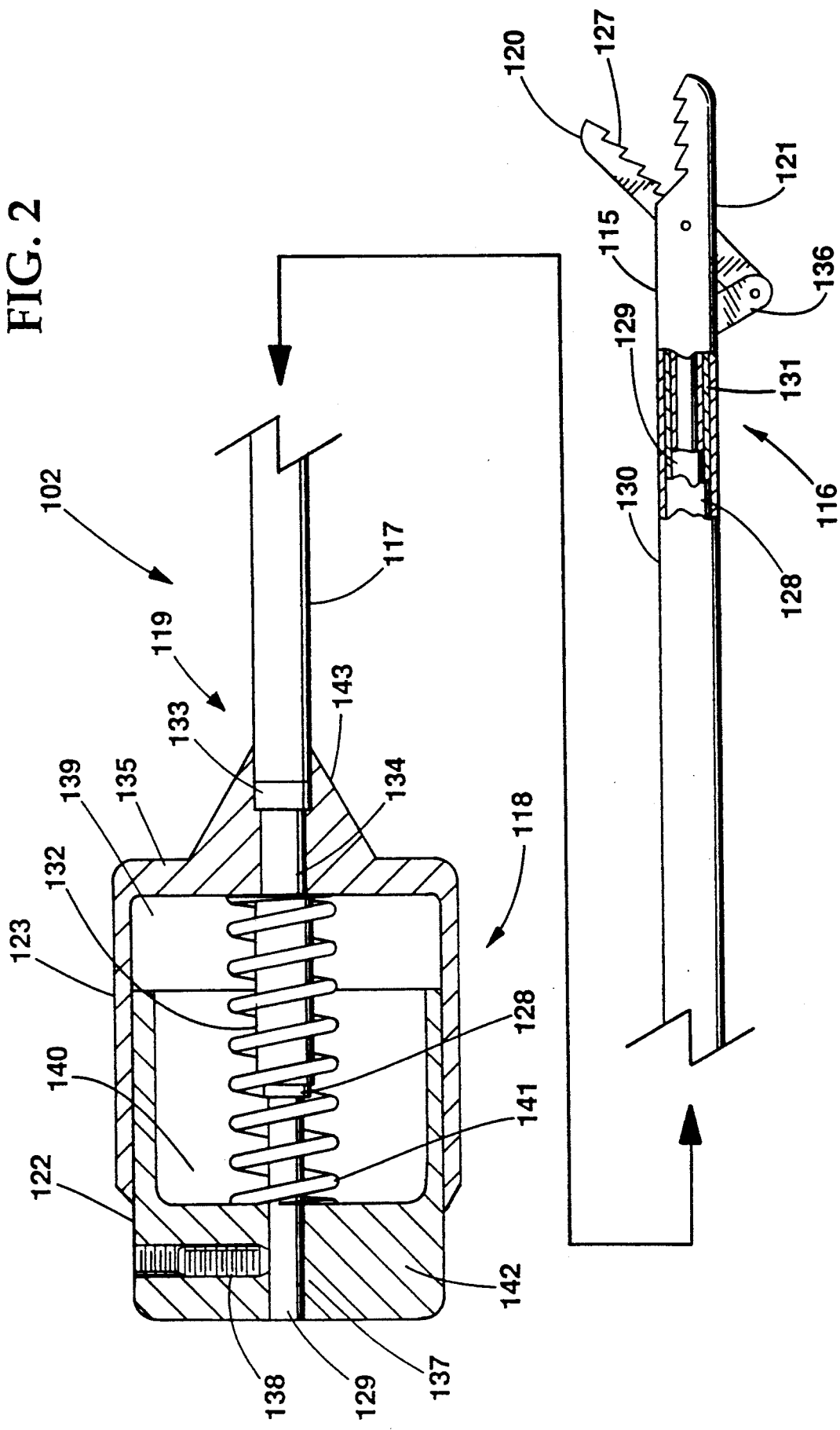
FIG. 2 depicts an enlarged, partially sectioned, side view of the retractor of FIG. 1.

Depicted in FIG. 2 is an enlarged, partially sectioned, side view of tissue retractor 102. Tissue retractor 102 includes needle-sized elongated member 117 with tissue grasper 115 positioned about distal end 116 and handle 118 positioned about distal end 119 thereof. Jaws 120 and 121 of the grasper are depicted in this figure in the open position with alligator teeth 127 positioned on opposing faces of the jaws. Elongated member 117 comprises an outer cannula 128, inner rod 129, and outer sheath 130. Outer cannula 128 comprises a 12.125" length of an 18.5 gauge regular wall tube with an outside diameter of approximately 0.46" and passage 131 extending longitudinally therethrough with an inside diameter of 0.030". Distal end 116 of the outer cannula is connected to stationary jaw 121. Proximal end 119 of the outer cannula is connected to handle enclosure 123 through passage 134 with proximal and distal retaining tubes 132 and 133 on opposite sides of enclosure wall 135, as shown.

Inner rod 129 comprises a 22 gauge thin-wall stainless steel tube with an outside diameter of approximately 0.028" and an inside diameter of approximately 0.014". A mandrel of stainless steel wire is inserted through the passage of the thin-wall tube and soldered about the proximal and distal ends thereof. Distal end 116 of the inner rod is connected to movable jaw 120 via interconnecting link 136 in a well-known manner. The proximal end of the inner rod is connected to push button piston 122 via passage 137 thereof and fixed thereto with a well-known set screw 138, as shown.

Handle 118 comprises machined, vinyl material enclosure 123 with cavity 139 formed therein, as shown. The handle further comprises machined, vinyl material push button piston 122 slidably positioned in cavity 139. Push button piston 122 also includes cavity 140 communicating with enclosure cavity 139. Positioned in cavity 139 of the enclosure and cavity 140 of the piston around outer cannula 128 and inner rod 129 is spring 141 engaging opposite facing walls 135 and 142 and providing expansion tension thereon. Spring 141 is commercially available as model number LC-0380-8 from Lee Spring, Inc., Des Plaines, Ill.

Handle enclosure 123 also includes outer shoulder 143 extending distally therefrom about proximal end 119 of elongated member 119. Passage 134 extends therethrough of which proximal and distal retaining tubes 132 and 133 are friction welded on outer cannula 128 on opposite sides of enclosure wall 135, as shown.

Elongated member 117 also includes outer sheath 130 comprising, for example, a nylon material tube having an outside dimension of 0.065" and an inside dimension of 0.050". Proximal end 119 of the nylon material outer sheath is glued to shoulder 143 of the handle enclosure next to distal retaining tube 133.

Handle enclosure 123 comprises a machined, vinyl material cylindrical cup with a length of approximately 0.750" and an overall length with outer shoulder 143 of approximately 1.000". The depth of enclosure cavity 139 is approximately 0.650". The outside diameter of the handle enclosure is approximately 0.750". The diameter of the cavity is approximately 0.650". Shoulder 143 has an outermost diameter of 0.250" with 15 degree tapered sides. Passage 134 is approximately 0.052" in diameter. The distal end of the shoulder is countersunk to accept 17 gauge thin-wall, stainless steel, distal retaining tube 133, which is approximately 0.04" in length. Proximal retaining tube 132 is a 17 gauge thin-wall, stainless steel tube approximately 0.300" in length. Outer sheath nylon tube 130 is approximately 5 French (0.066") in diameter.

Handle 118 assumes operated and relaxed states corresponding to the open and closed positions of grasper 115. With spring 141 engaging the push button and handle enclosure, the handle assumes the relaxed state with the grasper in the closed position. To operate the handle to the operated state, the physician grasps handle enclosure 123 with the middle and index fingers and depresses push button 122 with the thumb. As a result, spring 141 is compressed and tissue grasper 115 and jaws 120 and 121 are operated to the open position. This is accomplished by inner rod 12 1. To operate the retractor to the closed position, the physician simply releases the push button. Spring 141 separates the push button and handle enclosure, causing jaws 120 and 121 to close. It is to be understood that the above-described percutaneously insertable needle-sized retractor and system is merely an illustrative embodiment of the principles of this invention and that other needle-sized retractors and systems may be devised by those skilled in the art without departing from the spirit and scope of this invention. It is contemplated that the tissue grasper at the distal end of the retractor may comprise other configurations such as a biopsy punch, normally opened rather than closed jaws, cutting blades, and the like. It is further contemplated that the handle may take on other shapes of which to operate the tissue grasper between open and closed positions. It is also contemplated that the materials of the grasper may comprise other well-known and commercially available materials.

What is claimed is:

1. A percutaneously insertable tissue retractor comprising:
    an outer cannula having a passage extending longitudinally therethrough, a proximal end and a distal end;
    an inner rod having a proximal end and a distal end and passing through said passage of said outer cannula;
    a tissue grasper positioned about said distal ends of said outer cannula and said inner rod and having open and closed positions, both of said outer cannula and said grasper in said closed position being sized for insertion through a needle-sized trocar sheath having an outside diameter in a range of 10 to 22 gauge;
    an enclosure connected to said proximal end of said outer cannula and having a cavity therein, a piston slidably positioned in said cavity and connected to said proximal end of said inner rod, and first and second states for operation of said grasper between said open and closed positions, respectively;
    a first retaining tube positioned on said outer cannula in said cavity of said enclosure; and
    a second retaining tube on said outer cannula outside of said cavity of said enclosure.

2. The retractor of claim 1 wherein said grasper includes first and second pivotedly interconnected jaws operable between said open and closed positions, said first jaw connected to said distal end of said outer cannula, said second jaw connected to said distal end of said inner rod.

3. The retractor of claim 1 wherein said handle further includes a spring positioned in said cavity engaging said enclosure and said piston.

4. The retractor system of claim 3 wherein said elongated member further includes an outer sheath connected to said handle and having a passage extending therethrough of which said outer cannula is positioned therein.

5. A percutaneously insertable retractor system comprising:
    a needle-sized trocar sheath having an outside diameter in a range of 10 to 22 gauge, a first distal end, a first proximal end, and a first passage extending longitudinally therethrough, said sheath comprising a retention cap positioned about said first proximal end of said sheath and having a second passage extending longitudinally therethrough and communicating with said first passage of said sheath, said retention cap also having a seal positioned about said second passage for fixedly positioning said stylet relative to said sheath when said stylet is inserted through said second passage of said cap and in said first passage of said sheath;
    a retention flange having a third passage therein for insertion of said sheath therethrough, said flange being movably and fixedly positionable about and along an outer surface of said sheath;
    a tissue retractor insertable through said first passage and extendable from said distal end of said trocar sheath, said retractor including an elongated member and a tissue grasper positioned about a distal end of said member, said member and said grasper being sized for insertion through said first passage of said sheath, said grasper including first and second pivotedly interconnected jaws operable between open and closed positions, said elongated member including an outer cannula having a fourth passage extending longitudinally therethrough and an inner rod passing through said fourth passage of said outer cannula, each of said rod and said outer cannula having a distal end connected to said grasper and a proximal end connected to a handle, said first jaw connected to said distal end of said outer cannula, said second jaw connected to said inner rod, said elongated member further including an outer sheath connected to said handle and having a passage extending longitudinally therethrough of which said outer cannula is positioned therein, said handle being positioned about a proximal end of said member, having first and second states for operating said grasper between said open and closed positions, respectively, and including an enclosure having a cavity therein and connected to said proximal end of said outer cannula and a piston slidably positioned in said cavity and connected to said proximal end of said inner rod, said handle further including a spring positioned in said cavity engaging said enclosure and said piston; and
    a trocar stylet having an outside diameter sized for insertion through said passage of said sheath, said trocar stylet including a pointed distal end that extends from said distal end of said sheath when said stylet is inserted through said passage of said sheath.

* * * * *